United States Patent [19]
Katou et al.

[11] Patent Number: 5,180,416
[45] Date of Patent: Jan. 19, 1993

[54] HERBICIDAL COMPOSITION COMPRISING A LIQUID THIOCARBAMATE HERBICIDE, A SOLID HERBICIDE, SURFACTANT, AND DRY PROCESS SILICIC ACID

[75] Inventors: Susumu Katou, Shizuoka; Kanji Nakamura, Shimizu, both of Japan

[73] Assignee: Kumiai Chemical Industry Co., Ltd., Tokyo, Japan

[21] Appl. No.: 623,658

[22] PCT Filed: May 23, 1990

[86] PCT No.: PCT/JP90/00655

§ 371 Date: Dec. 31, 1990

§ 102(e) Date: Dec. 31, 1990

[87] PCT Pub. No.: WO90/14010

PCT Pub. Date: Nov. 29, 1990

[30] Foreign Application Priority Data

May 23, 1989 [JP] Japan .................................. 1-129284

[51] Int. Cl.$^5$ .................. A01N 43/34; A01N 43/54; A01N 37/00; A01N 25/22
[52] U.S. Cl. .................. 504/136; 71/DIG. 1; 504/143; 504/139; 504/129
[58] Field of Search ............... 71/92, 100, DIG. 1, 71/94, 88, 95

[56] References Cited

U.S. PATENT DOCUMENTS 4,599,104  7/1986  Nagano et al. .................. 71/92
4,921,527  5/1990  Tseng .................................. 71/92

FOREIGN PATENT DOCUMENTS 0043564  1/1982  European Pat. Off. .
0089268  9/1983  European Pat. Off. .
54-11368  5/1979  Japan .
57-2202   1/1982  Japan .

*Primary Examiner*—Carolyn Elmore
*Assistant Examiner*—S. Mark Clardy
*Attorney, Agent, or Firm*—Oblon, Spivak, McClelland, Maier & Neustadt

[57] ABSTRACT

The present invention discloses a complex suspended herbicide formulation including: a herbicidally active ingredient of thiolcarbamate type which is liquid at common temperature; a solid herbicidally active ingredient which is slightly soluble in the herbicidally active ingredient of thiolcarbamate type at common temperature; a surfactant; and a dry process white carbon; wherein the solid herbicidally active ingredient is dispersed and suspended in the herbicidally active ingredient of thiolcarbamate type in the presence of the surfactant and the dry process white carbon; and wherein the herbicidally active ingredient of thiolcarbamate type is represented by the formula:

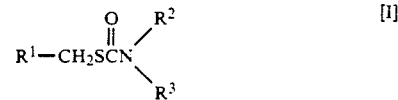

wherein $R^1$ is an alkyl group having from 1 to 3 carbon atoms, a phenyl group, or a halogen-substituted phenyl group; $R^2$ and $R^3$ are alkyl groups having from 1 to 5 carbon atoms, with the proviso that $R^2$ and $R^3$ may form a ring.

5 Claims, No Drawings

HERBICIDAL COMPOSITION COMPRISING A LIQUID THIOCARBAMATE HERBICIDE, A SOLID HERBICIDE, SURFACTANT, AND DRY PROCESS SILICIC ACID

FIELD OF THE INVENTION

The present invention relates to a complex suspended herbicide formulation without an organic solvent which is useful for controlling agriculturally hazardous weeds.

BACKGROUND OF THE INVENTION

As thiolcarbamate herbicides, commercial products are available such as those known by common names Thiobencarb, Orbencarb, Esprocarb, Molinate, EPTC, and the like, and they are very useful for controlling gramineous weeds which are strongly hazardous weeds. In addition, it has been known that a complex formulation, comprising a thiolcarbamate herbicide and an active ingredient for controlling broadleaf weeds, galingale weeds or the like, is a labor saving herbicide which exhibits a wide spectrum for controlling weeds.

These formulations including thiolcarbamate herbicides are used mainly in the form of granules for direct application and in the form of emulsifiable concentrates to be diluted for use.

Conventional emulsifiable concentrates are prepared usually by employing an organic solvent and a surfactant with an active ingredient. In general, a herbicidally active ingredient of thiolcarbamate type has a low melting point and most of the herbicidally active ingredients are liquid at common temperature. In addition, another herbicidally active ingredient to be mixed with that of thiolcarbamate type may be equivalent to various ingredients such as a liquid ingredient being compatible with that of thiolcarbamate type and a solid ingredient being slightly soluble therein. In the case where said another ingredient is slightly soluble in the herbicidally active ingredient of thiolcarbamate type, an organic solvent has to be blended thereinto. However, use of an organic solvent brings about various problems including a safety problem to the users of the agricultural chemical because of the phytotoxicity of the organic solvent, a storage problem due to the inflammability of the organic solvent, an environmental pollution problem by its application, a phytotoxicity to crop plants, and the like. Furthermore, in order to emulsify and disperse not only the active ingredient but also the organic solvent used, a surfactant is employed in a large amount, whereby there will be an economical problem as well as a problem of environmental pollution due to the surfactant.

Therefore, for an emulsifiable concentrate, it is desired to essentially solve the above-mentioned various problems attributable to the organic solvent and the surfactant.

A wettable powder and a flowable formulation are conceivable as the types of formulation which may be substituted for the emulsifiable concentrate. However, the wettable powder has a problem of dusting at the time of dilution, and there is a possible danger to the safety of the users. Besides, in the case of a liquid activate ingredient, it is difficult to obtain a highly concentrated formulation as compared with the emulsifiable concentrate. A granulated wettable powder has also been proposed to prevent dusting at the time of dilution, but in the case where the active ingredient is liquid, such a method still has a drawback, that it is difficult to obtain a formulation having a high concentration. On the other hand, a flowable formulation, prepared by having a solid active ingredient suspended and dispersed in water or having a liquid active ingredient emulsified and dispersed in water, usually contains an organic solvent such as ethylene glycol, propylene glycol, or the like in order to impart freeze resistance. Accordingly, it has a problem attributable to such an organic solvent. In addition, it has a problem that the freeze resistance is inadequate in an extremely cold area of −20° C. or lower, whereby it freezes, and when returned to common temperature, the dispersion system will be destroyed, and separation or precipitation will result. Furthermore, in many cases, a flowable formulation is adjusted to have a high viscosity to improve the storage stability at common temperature, whereby the handling at the time of use often tends to be difficult.

As a conventional art to obtain an emulsifiable concentrate without using an organic solvent, there is a non-solvent type of a highly concentrated emulsifiable concentrate (Japanese Patent Application Second Publication No. 53-45370) or an emulsifying agent for an emulsifiable concentrate of an agricultural chemical without using an organic solvent (Japanese Patent Application Second Publication No. 63-39561). By using the art, an emulsifiable concentrate comprising a herbicidally active ingredient of thiolcarbamate type and another herbicidally active ingredient which can be dissolved in the herbicidally active ingredient of thiolcarbamate type may be obtained. However, when said another herbicidally active ingredient, which is slightly soluble solid, cannot be dissolved in a herbicidally active ingredient of thiolcarbamate type, the slightly soluble solids are precipitated after formulation, whereby the desired storage stability cannot be obtained.

As a conventional art to dissolve an agricultural chemical ingredient in a hydrophobic solvent and to suspend another agricultural chemical ingredient which is slightly soluble therein, there is a complex agricultural chemical composition (Japanese Patent Application First Publication No. 57-2202). The complex composition includes an organic solvent, whereby it has above-mentioned problems due to an organic solvent. In addition, little amount of the slightly soluble agricultural chemical ingredient included in the complex composition causes drawbacks such that a stabilized suspension cannot be obtained and the desired storage stability may not be obtained.

As a conventional art to disperse and suspend a herbicidally active solid ingredient, which is slightly soluble, in a solution of water-soluble herbicidally active ingredient in the presence of a surfactant, a water suspension type of a complex herbicide (Japanese Patent Application Second Publication No. 63-37761) is known. However, it is impossible to formulate a herbicidally active ingredient of thiolcarbamate type by using this art because the herbicidally active thiolcarbamate ingredient is slightly soluble in water.

As a conventional art to disperse uniformly in water or an organic solvent, which is slightly soluble in water, an organic solvent, or a liquid agricultural chemical, an agricultural chemical, in order to improve a storage stability thereof, there is a suspensibility agricultural chemical dissemination agent (Japanese Patent Application Second Publication No. 54-11368). It is possible to formulate a herbicidally active ingredient of thiolcarbamate type by mixing fine powders of colloidal aluminum silicate hydrate and an organic solvent such as a glycol solvent and the like in accordance with the embodiments described in the Japanese patent application. This art has a drawback such as using an organic solvent therein, and therefore, does not contribute to resolving the problems of an organic solvent.

Therefore, in order to obtain a complex herbicide formulation, which includes a herbicidally active thiolcarbamate ingredient useful for controlling agriculturally hazardous gramineous weeds so as to have a wide spectrum for controlling weeds, it is strongly desired to develop an agricultural chemical formulation comprising a herbicidally active ingredient of thiolcarbamate type and another solid herbicidally active ingredient, which is slightly soluble in the herbicidally active thiolcarbamate ingredient, wherein said another solid herbicidally active ingredient is suspended and dispersed in said herbicidally active ingredient of thiolcarbamate type, so as to be diluted and applied without the above-mentioned problems with respect to an organic solvent and a surfactant.

DESCRIPTION OF THE INVENTION

It is ideal that a herbicidally active ingredient of thiolcarbamate type, which is liquid at common temperature, and another solid herbicidally active ingredient, which is slightly soluble in the herbicidally active thiolcarbamate ingredient at common temperature, can be stably suspended and dispersed each other without using an organic solvent and a surfactant. However, a herbicidally active ingredient of thiolcarbamate type is slightly soluble in water, and it is difficult to dissolve or disperse the herbicidally active thiolcarbamate ingredient in water by itself. Accordingly, it is an object of the present invention to provide a formulation having a stably excellent emulsifiability under various application conditions, such as a wide range of dilution, various qualities of water used for dilution and various temperatures of water, by addition of a very small amount of a surfactant and a precipitation-preventive agent, per unit weight of the agricultural chemical.

PREFERRED EMBODIMENTS OF THE INVENTION

The present inventors have conducted extensive researches to overcome the above-mentioned problems, by formulating a good emulsifiable concentration including a herbicidally active ingredient of thiolcarbamate type which is liquid at common temperature, and another solid herbicidally active ingredient which is slightly soluble in the herbicidally active thiolcarbamate ingredient at common temperature, wherein the solid herbicidally active ingredient is dispersed and suspended in the herbicidally active ingredient of thiolcarbamate type. As a result, the present inventors have found that in a herbicidally active ingredient of thiolcarbamate type which is liquid at common temperature, another solid herbicidally active ingredient which is slightly soluble in the herbicidally active thiolcarbamate ingredient at common temperature can be stably suspended without using an organic solvent or water only by means of adding a very small amount of a surfactant and a dry process white carbon as a precipitation preventive agent to the mixture of the active ingredients, whereby the formulation thereof exhibits a good emulsifiable concentrate.

According to the present invention, there is provided a complex suspended herbicide formulation wherein a surfactant and a dry process white carbon as a precipitation-preventive agent are blended into a complex agricultural chemical composition obtained by dispersing and suspending in a herbicidally active ingredient of thiolcarbamate type which is liquid at common temperature, another solid herbicidally active ingredient which is slightly soluble in the herbicidally active thiolcarbamate ingredient at common temperature.

Now, the present invention will be described in detail with reference to the preferred embodiments. The herbicidally active ingredient of thiolcarbamate type which is liquid at common temperature according to the present invention is shown as the following formula [I]:

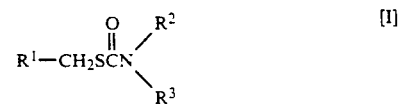

wherein $R^1$ is an alkyl group having from 1 to 3 carbon atoms, a phenyl group, or a halogen-substituted phenyl group, $R^2$ and $R^3$ are alkyl groups having from 1 to 5 carbon atoms, with the proviso that $R^2$ and $R^3$ may form a ring.

The compound represented by the formula [I] includes the following compounds. The compound Nos. will be referred to hereinafter.

Compound (1): S-(4-chlorobenzyl)-N,N-diethylthiolcarbamate (common name: Thiobencarb)

Compound (2): S-(2-chlorobenzyl)-N,N-diethylthiolcarbamate (common name: Orbencarb)

Compound (3): S-benzyl=1,2-dimethylpropyl(methyl)-thiolcarbamate (common name: Esprocarb)

Compound (4): S-ethyl-hexahydro-1H-azepine-1-carbothioate (common name: Molinate)

Compound (5): S-ethyl-N,N-di-n-propylthiolcarbamate (common name: EPTC).

As a herbicidally active ingredient solid which is slightly soluble in the liquid herbicidally active thiolcarbamate ingredient at common temperature, a herbicidally active ingredient of diphenyl ether type such as 2,4,6-trichlorophenyl-4-nitrophenyl ether, 2,4-dichlorophenyl-4-nitro-3-methoxyphenyl ether, or the like; a herbicidally active ingredient of pyrazol type such as 4-(2,4-dichlorobenzoyl)-1,3-dimethyl-5-pyrazolyl-p-toluenesulfonate, 2-[4-(2,4-dichlorobenzoyl)-1,3-dimethylpyrazol-5-yloxy]acetophenone, or the like; a herbicidally active ingredient of amide type such as (RS)-2-bromo-N-(α,α-dimethylbenzyl)-3,3-dimethylbutylamide, or the like; a herbicidally active ingredient of sulfonylurea type such as methyl=α-(4,6-dimethoxypyrimidin-2-ylcarbamoylsulfamoyl)-o-toluate, ethyl-5-[3-(4,6-dimethoxypyrimidin-2-)ureidosulfonyl]-1-methylpyrazol-4-carboxylate, or the like; a herbicidally active ingredient of phenoxy type such as α-(2-naphthoxy)-2-propionanilide, or the like; a herbicidally active ingredient of diadinone type such as 3-isopropyl-2,1,3-benzo-thiadinone-(4)-2,2-dioxide; or the like can be used but the herbicidally active ingredient solid is not restricted to such specific ingredients mentioned above.

A suitable surfactant must be blended into the herbicidally active thiolcarbamate ingredient in order to emulsify and disperse in water the herbicidally thiolcarbamate active ingredient, which is slightly soluble in water, and to suspend and disperse in water another solid herbicidally active ingredient, which is slightly soluble in the herbicidally active thiolcarbamate ingredient. Since a surfactant depends on a kind of herbicidally active ingredients, it is important to select the suitable surfactant. A surfactant of the present invention may be equivalent to those generally used in an agricultural chemical formulation field. A useful surfactant includes a non-ionic surfactant such as polyoxyethylene allyl ether, polyoxyalkylene styrylphenyl ether, polyoxyethylene solbitanealkylate, polyoxyethylene glycol, polyoxyethylene alkyl ester, polyoxyalkylene glycol, or the like, and an anion surfactant such as ligninsulfonate, alkylallylsulfonate, dialkylallylsulfonate, polyoxyethylene alkylallylphosphate, polyoxyethylene alkylallylethersulfate, alkylallylsulfonate, polyoxyethylene styrylphenylethersulfate, or the like. The surfactants are not restricted to such specific examples. In addition, these surfactants may be used alone or in combination with at least two these surfactants and the mixture ratio thereof may be arbitrarily selected. Although the mixing amount of the surfactants is not specially determined, the surfactants are used in an amount of 3-20 parts by weight, preferably in an amount of 5-10 parts by weight, per 100 parts by weight of the complex suspended herbicide formulation according to the present invention.

In order to enhance the storage stability of the herbicidally active ingredient which is solid and slightly soluble in the liquid herbicidally active ingredient of thiolcarbamate type at common temperature, both the surfactant having a dispersion effect and the dry process white carbon must be blended thereinto, whereby thixotropy can be obtained and precipitation of the solid materials is completely avoided. The dry process white carbon is a fine grain silicic acid produced by pyrolysis of halogenated silicon, a material containing silicic acid, or an organosilicon compound. The dry process white carbons include the following materials:

(1) a material produced by pyrolysis (thermal decomposition method, vapor phase method) of halogenated silicon, for example, fine grain of silicic acid obtained by subjecting the mixture of halogenated silicon such as tetrachloro silicon or the like, hydrogen, and oxygen (air) which has prescribed ratio thereof to combustion at the temperature of 1000°-1200° C.;

(2) a material produced by pyrolysis of a material containing silicic acid, for example, fine grain of silicic acid obtained by heating and subjecting a material containing silicic acid such as quartz rock, quartz sand, clay, or the like to reduction in the presence of a carbon donor such as coke, anthoracite, or the like by arc at approximately 2000° C.;

(3) a material produced by pyrolysis of an organosilicon compound, for example, fine grain silicic acid obtained by pyrolyzing an organic silicon compound such as various silicic acid esters, ethyl silinate, or the like.

Among the dry process white carbons mentioned above, particularly the materials designated (1) and (2) are desirable. In addition, other materials may be employed as a dry process white carbon. The dry process white carbons may be used alone or in combination with two or more other materials.

Dry process white carbons have properties such that the purity of silicon oxide is extremely high, and adsorption moisture content is extremely small in comparison with wet process white carbon (white carbon produced by wet process). Heretofore, a wet process white carbon is used as a diluent such as a dusting powder or a wettable powder or as a precipitation-preventive agent such as a water suspension agent. However, the wet process white carbons do not have a precipitation-preventive effect in the system without an organic solvent and water as shown in the tests described hereafter.

Although the amount of the dry process white carbon is not especially restricted, the dry process white carbon is used in an amount of 0.01-10 parts by weight per 100 parts by weight of the complex suspended herbicide formulation according to the present invention, preferably in an amount of 0.5-5 parts by weight.

The complex suspended herbicide formulation according to the present invention may optionally include a herbicidally active ingredient which is dissolved in the herbicidally active ingredient of thiolcarbamate type or supplements such as a solidifying temperature depressent (for example, a phenol compound such as bisphenol A, resorcin, or the like), and ingredient stabilizer, and the like, as the case requires. In addition, although the complex suspended herbicide formulation according to the present invention is intended to include no organic solvents, an organic solvent which has no harm to men and animals and has a high flash point may be blended into the complex suspended herbicide in order to adjust the physical characteristics thereof such as viscosity and specific gravity thereof. The viscosity controlling agent which may be blended into the complex suspended herbicide formulation includes, for example, a vegetable oil such as soy bean oil, rape seed oil, or the like and a mineral oil such as liquid paraffin, n-paraffin, or the like.

The preferable method for suspending and dispersing a herbicidally active ingredient, which is solid and slightly soluble, in the liquid herbicidally active ingredient of thiolcarbamate type at common temperature may comprise the steps of: blending into a herbicidally active ingredient of thiolcarbamate type, another herbicidally active ingredient which is solid and slightly soluble in the herbicidally active ingredient of thiolcarbamate type, a surfactant, and a dry process white carbon; and pulverizing the mixture by a sandgrinder, a die mill, a ball mill, or the like. In addition, before the blending step, the solid and slightly-soluble herbicidally active ingredient may be pulverized by Jet-O-Mizer or the like so as to have an average particle diameter of approximately 2 $\mu$m and below, and then the pulverized solid herbicidally active ingredient may be suspended and dispersed in the herbicidally active ingredient of thiolcarbamate type, which is blended with the surfactant and the dry process white carbon, by a homogenizer or the like.

The present invention will be described in detail with reference to Examples. However, it should be understood that the present invention is by no means restricted to such specific Examples. Specific examples of the white carbon used in Examples or to be used in the present invention will be presented in Table 1. In Table 1, "dry process" means 'a dry process white carbon', "wet process" means 'a wet process white carbon', and "process (1) or process (2)" means that the white carbon is produced by process (1) or process (2) described above. (In these Examples, "parts" means "parts by weight".)

TABLE 1

| Trademark | Manufactured by | Kind | Process |
|---|---|---|---|
| Aerosil #130 | Nippon Aerosil Co., Ltd. | Dry process | (1) |
| Aerosil #200 | Nippon Aerosil Co., Ltd. | Dry process | (1) |

TABLE 1-continued

| Trademark | Manufactured by | Kind | Process |
|---|---|---|---|
| Aerosil #380 | Nippon Aerosil Co., Ltd. | Dry process | (1) |
| Aerosil R-972 | Nippon Aerosil Co., Ltd. | Dry process | (1) |
| Cab-O-Sil M-5 | Godfrey L. Cabot, Inc. | Dry process | (1) |
| Fransil-251 | Fransol | Dry process | (2) |
| Franteg | Franterre, S. A | Dry Process | (2) |
| Carplex #80 | Shionogi & Co., Ltd. | Wet Process | — |
| Tokusil N | Tokuyama Soda Co., Ltd. | Wet Process | — |
| Vitasil #220 | Taki Chemical Co., Ltd. | Wet Process | — |

EXAMPLE

Example 1

Sixty parts of Compound (1), 30 parts of 2,4,6-trichlorophenyl-4-nitrophenyl ether (common name: CNP), 2 parts of Aerosil #130, 6 parts of polyoxyethylene styrylphenyl ether, and 2 parts of dodecylbenzenesulfonic acid, calcium salt were mixed and pulverized by a sandgrinder. Glass beads were removed from the pulverized mixture to obtain a complex suspended herbicide formulation according to the present invention.

Example 2

Sixty parts of Compound (1), 30 parts of 4-(2,4-dichlorobenzoyl)-1,3-dimethyl-5-pyrazolyl-p-toluenesulfonate (common name: Pyrazolate), 2 parts of Aerosil #380, 4 parts of polyoxyethylene styrylphenyl ether, 2 parts of polyoxyethylene nonylphenyl ether, and 2 parts of dodecylbenzenesuolfonic acid, calcium salt were mixed and pulverized by a sandgrinder. Glass beads were removed from the pulverized mixture to obtain a complex suspended herbicide formulation according to the present invention.

Example 3

Sixty parts of Compound (1), 30 parts of α-(2-naphthoxy)-2-propionanilide (common name: Naproanilide), 2 parts of Fransil-251, 4 parts of polyoxyethylene styrylphenyl ether, one part of polyoxyethylene nonylphenyl ether, and 3 parts of dodecylbenzenesulfonic acid, calcium salt were mixed and pulverized by a sandgrinder. Glass beads were removed from the pulverized mixture to obtain a complex suspended herbicide formulation according to the present invention.

Example 4

Ninety parts of Compound (1), 3 parts of methyl=α-(4,6-dimethoxypyrimidin-2-ylcarbamoylsulfamoyl-o-toluate (common name: Bensulfuron methyl), 2 parts of Aerosil #200, 3.5 parts of polyoxyethylene styrylphenyl ether, and 1.5 parts of dodecylbenzenesulfonic acid, calcium salt were mixed and pulverized by a sandgrinder. Glass beads were removed from the pulverized mixture to obtain a complex suspended herbicide formulation according to the present invention.

Example 5

Sixty parts of Compound (1), 2 parts of methyl=α-(4,6-dimethoxypyrimidin-2-ylcarbamoylsulfamoyl-o-toluate (common name: Bensulfuron methyl), 4 parts of Aerosil #200, 7 parts of polyoxyethylenated castor oil, 3 parts of dodecylbenzenesulfonic acid, calcium salt, and 24 parts of soy bean oil were mixed and pulverized by a sandgrinder. Glass beads were removed from the pulverized mixture to obtain a complex suspended herbicide formulation according to the present invention.

Example 6

Sixty parts of Compound (1), 2 parts of methyl=α-(4,6-dimethoxypyrimidin-2-ylcarbamoylsulfamoyl)-o-toluate (common name: Bensulfuron methyl), 4 parts of Aerosil #200, 4 parts of polyoxyethylene styrylphenyl ether, 3 parts of polyoxyethylene sorbitan monooleate, 3 parts of dodecylbenzenesulfonic acid, calcium salt, and 24 parts of n-paraffin were mixed and pulverized by a sandgrinder. Glass beads were removed from the pulverized mixture to obtain a complex suspended herbicide formulation according to the present invention.

Example 7

Sixty parts of Compound (4), 30 parts of 2,4,6-trichlorophenyl-4-nitrophenyl ether (common name: CNP), 1.5 parts of Aerosil #130, 5.5 parts of polyoxyethylene styrylphenyl ether, and 3 parts of dodecylbenzenesulfonic acid, calcium salt were mixed and pulverized by a sandgrinder. Glass beads were removed from the pulverized mixture to obtain a complex suspended herbicide formulation according to the present invention.

Example 8

Ninety parts of Compound (4), 3 parts of methyl=α-(4,6-dimethoxypyrimidin-2-ylcarbamoylsulfamoyl)-o-toluate (common name: Bensulfuron methyl), 2 parts of Aerosil #380, 3.5 parts of polyoxyethylene styrylphenyl ether, and 1.5 parts of dodecylbenzenesulfonic acid, calcium salt were mixed and pulverized by a sandgrinder. Glass beads were removed from the pulverized mixture to obtain a complex suspended herbicide formulation according to the present invention.

Comparative Example 1

Sixty-one parts of Compound (1), 30 parts of 2,4,6-trichlorophenyl-4-nitrophenyl ether (common name: CNP), 6 parts of polyoxyethylene styrylphenyl ether, and 3 parts of dodecylbenzenesulfonic acid, calcium salt were mixed and pulverized by a sandgrinder. Glass beads were removed from the pulverized mixture to obtain a comparative suspended herbicide formulation. (An example of employing no dry process white carbon.)

Comparative Example 2

Sixty parts of Compound (1), 30 parts of 2,4,6-trichlorophenyl-4-nitrophenyl ether (common name: CNP), 2 parts of Carplex #80, 6 parts of polyoxyethylene styrylphenyl ether, and 2 parts of dodecylbenzenesulfonic acid, calcium salt were mixed and pulverized by a sandgrinder. Glass beads were removed from the pulverized mixture to obtain a comparative suspended herbicide formulation. (An example employing a wet process white carbon.)

Comparative Example 3

Thirty parts of Compound (1), 15 parts of 2,4,6-trichlorophenyl-4-nitrophenyl ether (common name: CNP), 6 parts of Sorpol 900A (a surfactant, manufactured by Toho Chemical Industry Company Limited), 6 parts of Sorpol 2401-D3 (a surfactant, manufactured by Toho Chemical Industry Company Limited), 6 parts of Pegurol HC-17 (a surfactant, manufactured by Toho Chemical Industry Company Limited), 27 parts of soy bean oil, and 10 parts of Kawakasol (solvent including methylnaphthalene as a main ingredient, manufactured by Kawasaki Kasei Chemicals Ltd.) were mixed and pulverized by a sandgrinder. Glass beads were removed from the pulverized mixture to obtain a comparative suspended herbicide formulation. (An example manufactured by the method described in Japanese Patent Application First Publication 57-2202.)

Comparative Example 4

Thirty parts of Compound (1), 15 parts of 2,4,6-trichlorophenyl-4-nitrophenyl ether (common name: CNP), 4 parts of polyoxyethylenealkyl ether, 4 parts of polyoxyethylene nonylphenyl ether, 4 parts of alkylbenzenesulfonic acid, sodium salt, 4 parts of ethylene glycol monobutyl ether, 3 parts of colloidal aluminum silicate, hydrate, fine powder, and 36 parts of water were mixed and pulverized by a sandgrinder. Glass beads were removed from the pulverized mixture to obtain a comparative suspended herbicide. (An example manufactured by the method described in Japanese Patent Application Second Publication No. 54-11368.)

Comparative Example 5

Thirty parts of Compound (1), 15 parts of 2,4,6-trichlorophenyl-4-nitrophenyl ether (common name: CNP), 4 parts of polyoxyethylene styrylphenyl ether, 2 parts of polyoxyethylene nonylphenyl ether, 2 parts of dodecylbenzenesulfonic acid, calcium salt, and 45 parts of xylene were mixed and dissolved to obtain a comparative emulsifiable concentrate herbicide formulation. (A general emulsifiable concentrate herbicide example.)

Comparative Example 6

Sixty parts of Compound (1), 4 parts of polyoxyethylene styrylphenyl ether, 2 parts of polyoxyethylene nonylphenyl ether, 2 parts of dodecylbenzenesulfonic acid, calcium salt, and 30 parts of xylene were mixed and dissolved to obtain a comparative emulsifiable concentrate herbicide formulation.

Now, the effects of the complex suspended herbicide formulation according to the present invention will be described with reference to Test Examples.

Test Example 1: Test for emulsifiability

Using a cylinder having a capacity of 250 ml and equipped with a stopper, the initial emulsifiability and the emulsified stability after reversing it 30 times for 1 minute and after being left to stand still for 2 hours and 24 hours, were examined under the following test conditions. The results are shown in Table 2 (temperature of water: 10° C.) and Table 3 temperature of water: 30° C.).

| (Test Conditions) | |
|---|---|
| Nature of water: | Hard water of 3°, hard water of 19.2° |
| Temperature of water: | 10° C., 30° C. |
| Degree of dilution: | 25 times, 250 times |

(Evaluation Method)

Initial emulsifiability
◯: Excellent self emulsifiability
Δ: Slightly poor self emulsifiability
X: Poor self emulsifiability
Emulsified stability
◯: No separation and precipitation
Δ: Separation and precipitation not more than 2 mm
X: Separation and precipitation not less than 2 mm

TABLE 2

| | Initial Emulsifiability | | | | Emulsified Stability | | | | | | | |
|---|---|---|---|---|---|---|---|---|---|---|---|---|
| | | | | | Hard Water of 3° | | | | Hard Water of 19.2° | | | |
| | Hard Water of 3° | | Hard Water of 19.2° | | After 2 hours | | After 24 hours | | After 2 hours | | After 24 hours | |
| Example No. | X25 | X250 | X25 | X250 | X25 | X250 | X25 | X250 | X25 | X250 | X25 | X250 |
| (Temperature of water: 10° C.) | | | | | | | | | | | | |
| Example 1 | ◯ | ◯ | ◯ | ◯ | ◯ | ◯ | ◯ | ◯ | ◯ | ◯ | ◯ | ◯ |
| Example 2 | ◯ | ◯ | ◯ | ◯ | ◯ | ◯ | ◯ | ◯ | ◯ | ◯ | ◯ | ◯ |
| Example 3 | ◯ | ◯ | ◯ | ◯ | ◯ | ◯ | ◯ | ◯ | ◯ | ◯ | ◯ | ◯ |
| Example 4 | ◯ | ◯ | ◯ | ◯ | ◯ | ◯ | ◯ | ◯ | ◯ | ◯ | ◯ | ◯ |
| Example 5 | ◯ | ◯ | ◯ | ◯ | ◯ | ◯ | ◯ | ◯ | ◯ | ◯ | ◯ | ◯ |
| Example 6 | ◯ | ◯ | ◯ | ◯ | ◯ | ◯ | ◯ | ◯ | ◯ | ◯ | ◯ | ◯ |
| Example 7 | ◯ | ◯ | ◯ | ◯ | ◯ | ◯ | ◯ | ◯ | ◯ | ◯ | ◯ | ◯ |
| Example 8 | ◯ | ◯ | ◯ | ◯ | ◯ | ◯ | ◯ | ◯ | ◯ | ◯ | ◯ | ◯ |
| Comparative Example 1 | ◯ | ◯ | ◯ | ◯ | Δ | ◯ | X | ◯ | Δ | ◯ | X | ◯ |
| Comparative Example 2 | ◯ | ◯ | ◯ | ◯ | ◯ | Δ | ◯ | X | ◯ | Δ | ◯ | X |
| Comparative Example 3 | ◯ | ◯ | ◯ | Δ | ◯ | Δ | X | X | Δ | X | X | X |
| Comparative Example 4 | ◯ | ◯ | ◯ | Δ | ◯ | Δ | X | X | Δ | X | X | X |
| Comparative Example 5 | ◯ | ◯ | ◯ | ◯ | ◯ | ◯ | ◯ | Δ | ◯ | ◯ | ◯ | Δ |
| Temperature of water: 30° C. | | | | | | | | | | | | |
| Example 1 | ◯ | ◯ | ◯ | ◯ | ◯ | ◯ | ◯ | ◯ | ◯ | ◯ | ◯ | ◯ |
| Example 2 | ◯ | ◯ | ◯ | ◯ | ◯ | ◯ | ◯ | ◯ | ◯ | ◯ | ◯ | ◯ |
| Example 3 | ◯ | ◯ | ◯ | ◯ | ◯ | ◯ | ◯ | ◯ | ◯ | ◯ | ◯ | ◯ |
| Example 4 | ◯ | ◯ | ◯ | ◯ | ◯ | ◯ | ◯ | ◯ | ◯ | ◯ | ◯ | ◯ |
| Example 5 | ◯ | ◯ | ◯ | ◯ | ◯ | ◯ | ◯ | ◯ | ◯ | ◯ | ◯ | ◯ |
| Example 6 | ◯ | ◯ | ◯ | ◯ | ◯ | ◯ | ◯ | ◯ | ◯ | ◯ | ◯ | ◯ |
| Example 7 | ◯ | ◯ | ◯ | ◯ | ◯ | ◯ | ◯ | ◯ | ◯ | ◯ | ◯ | ◯ |
| Example 8 | ◯ | ◯ | ◯ | ◯ | ◯ | ◯ | ◯ | ◯ | ◯ | ◯ | ◯ | ◯ |
| Comparative Example 1 | ◯ | ◯ | ◯ | ◯ | Δ | ◯ | X | ◯ | Δ | ◯ | X | ◯ |
| Comparative | ◯ | ◯ | ◯ | ◯ | ◯ | Δ | ◯ | X | ◯ | Δ | ◯ | X |

TABLE 2-continued

| Example No. | Initial Emulsifiability | | | | Emulsified Stability | | | | | | | |
|---|---|---|---|---|---|---|---|---|---|---|---|---|
| | Hard Water of 3° | | Hard Water of 19.2° | | Hard Water of 3° | | | | Hard Water of 19.2° | | | |
| | | | | | After 2 hours | | After 24 hours | | After 2 hours | | After 24 hours | |
| | X25 | X250 | X25 | X250 | X25 | X250 | X25 | X250 | X25 | X250 | X25 | X250 |
| Example 2 Comparative Example 3 | ○ | ○ | ○ | Δ | Δ | Δ | X | X | Δ | X | X | X |
| Comparative Example 4 | ○ | ○ | ○ | Δ | Δ | Δ | X | X | Δ | X | X | X |
| Comparative Example 5 | ○ | ○ | ○ | ○ | ○ | Δ | ○ | Δ | ○ | Δ | ○ | Δ |

As shown in Table 2 and 3, the products of the present invention are superior in the initial emulsifiability and the emulsified stability to a conventional Comparative Examples 1-4.

Test Example 2: Test for freeze resistance and heat resistance

Samples formulated in examples were put in glass bottles having a capacity of 500 ml and stored at −25° C., −5° C., and 40° C. for 30 days. Then, they were left to stand at common temperature (25° C.) for 6 hours. Therefore, the changes in color and outer appearance and initial emulsifiabilities were examined. The results are shown in Table 4. Evaluation method Initial emulsifiability (hard water of 3°, diluted 100 times)

○: Excellent self emulsifiability
Δ: Slightly poor self emulsifiability
X: Poor self emulsifiability

TABLE 4

| Example No. | Change in color and outer appearance | | | Initial emulsifiability | | |
|---|---|---|---|---|---|---|
| | −25° C. 30 days | −5° C. 30 days | 40° C. 30 days | −25° C. 30 days | −5° C. 30 days | 40° C. 30 days |
| Example 1 | good | good | good | ○ | ○ | ○ |
| Example 2 | good | good | good | ○ | ○ | ○ |
| Example 3 | good | good | good | ○ | ○ | ○ |
| Example 4 | good | good | good | ○ | ○ | ○ |
| Example 5 | good | good | good | ○ | ○ | ○ |
| Example 6 | good | good | good | ○ | ○ | ○ |
| Example 7 | good | good | good | ○ | ○ | ○ |
| Example 8 | good | good | good | ○ | ○ | ○ |
| Comparative Example 1 | good | precipitation | precipitation | ○ | Δ | Δ |
| Comparative Example 2 | good | precipitation | precipitation | ○ | Δ | Δ |
| Comparative Example 3 | good | precipitation | precipitation and separation | Δ | X | X |
| Comparative Example 4 | separation | precipitation | precipitation and separation | X | X | X |
| Comparative Example 5 | crystals precipitation | good | good | Δ | ○ | ○ |

As shown in Table 4, the freezing resistance and heat resistance of the products of the present invention are excellent as compared with a conventional one according to Comparative Examples 1-5.

Test Example 3: Test for biological effects (1) Test for phytotoxicity

Into a 1/500 a container filled with paddy field soil, water was added to the depth of 3 cm. Eight bunches of the rice plants of 2.0-2.2 leaf stage, each bunch having two rice plants, were transplanted at the soil depth of 2 cm. On the 3rd day from transplanting, each composition described in Examples and Comparative Examples was diluted with water to a prescribed concentration and applied to the flooding water by drop treatment by means of a pipet. On the 30th day from the treatment, the phytotoxicity thereof was evaluated according to the evaluation standards described in Table 5. The test results are shown in Table 6.

(2) Test for herbicidal effects

In 1/500 a containers filled with paddy field soil, seeds of Echinochloa crus-galli and Scirpus juncoides were seeded separately. Four germinated plants of each of Sagittaria pygmaea and Cyperus serothinus were planted in the container separately. After the barnyard grass was in 2.0-2.2 leaf stage, water was added to the container to the depth of 3 cm. Each composition described in Examples and Comparative Examples was diluted with water to a prescribed concentration and applied to the flooding water by drop treatment by means of a pipet. On the 30th day from the treatment, the herbicidal effects were evaluated according to the evaluation standards described in Table 5. The test results are shown in Table 6. The herbicide treatment was given to the plants in the following leaf stages:

| Plants common name (Plants scientific name) | Leaf stage |
|---|---|
| Barnyard grass (Echinochloa crus-galli) | 2.0-2.2 |
| Bulrush (Scirpus juncoides) | 2.0-2.2 |

TABLE 5 -continued

| Plants common name (Plants scientific name) | Leaf stage |
|---|---|
| Narrowleaf arrowhead (*Sagittaria pygmaea*) | 2.0–3.0 |
| Flatsedge (*Cyperus serothinus*) | 2.0 |

TABLE 5

| Index | Phytotoxicities and herbicidal effects |
|---|---|
| 0 | No herbicidal effects (No phytotoxicities) |
| 1 | Herbicidal effects more than 0% and less than 30%. (Phytotoxicities) |
| 2 | Herbicidal effects not less than 30% and less than 50%. (Phytotoxicities) |
| 3 | Herbicidal effects not less than 50% and less than 70%. (Phytotoxicities) |
| 4 | Herbicidal effects not less than 70% and less than 90%. (Phytotoxicities) |
| 5 | Herbicidal effects not less than 90%. (Phytotoxicities) |

TABLE 6

| Formula No. | Compound (1) dose of active ingredient (g/10a) | Phytotoxicity index Rice | Herbicidal effective index | | | |
|---|---|---|---|---|---|---|
| | | | Echinochloa crus-galli | Scirpus iuncoides | Sagittaria pygmaea | Cyperus serothinus |
| Example 1 | 150 | 0 | 5 | 4 | 3 | 4 |
| | 300 | 0 | 5 | 5 | 5 | 5 |
| Example 2 | 150 | 0 | 5 | 4 | 4 | 4 |
| | 300 | 0 | 5 | 5 | 5 | 5 |
| Example 3 | 150 | 0 | 5 | 5 | 5 | 4 |
| | 300 | 0 | 5 | 5 | 5 | 5 |
| Example 4 | 150 | 0 | 5 | 5 | 5 | 5 |
| | 300 | 0 | 5 | 5 | 5 | 5 |
| Example 5 | 150 | 0 | 5 | 5 | 5 | 5 |
| | 300 | 0 | 5 | 5 | 5 | 5 |
| Example 6 | 150 | 0 | 5 | 5 | 5 | 4 |
| | 300 | 0 | 5 | 5 | 5 | 5 |
| Comparative Example 4 | 150 | 0 | 5 | 2 | 1 | 2 |
| | 300 | 2 | 5 | 4 | 3 | 4 |
| Comparative Example 5 | 150 | 0 | 5 | 3 | 2 | 3 |
| | 300 | 3 | 5 | 5 | 4 | 5 |
| Comparative Example 6 | 150 | 0 | 5 | 0 | 0 | 0 |
| | 300 | 1 | 5 | 2 | 1 | 2 |
| Non-treated region | — | 0 | 0 | 0 | 0 | 0 |

As shown in Table 6, the biological effects of the products according to the present invention are excellent as compared with an emulsifiable concentrate (Comparative Examples 5 and 6) and a conventional oil-in-water type suspension (Comparative Example 4).

Industrial Utility

The complex suspended herbicide formulation according to the present invention has a good emulsified stability without being affected by degree of dilution, nature of water, temperature of water, and the like. In addition, even if the herbicide formulation is frozen below its freezing temperature, the herbicide formulation has superior advantages such that the separation and precipitation thereof are not observed and the deterioration of emulsifiability is not observed after the frozen herbicide formulation is allowed to come to common temperature.

The complex suspended herbicide formulation according to the present invention does not have any problems including danger due to inflammability during the preparation thereof, and a hazardous problem to men and animals due to an organic solvent in comparison with a conventional emulsifying and flowable agents employing an organic solvent since the herbicide formulation of the present invention does not include any organic solvents. Therefore, as the herbicide formulation of the present invention can avoid inflammability in the case of transporting or storing the herbicide products, the users can safely use it. Furthermore, the herbicide formulation according to the present invention has a superior selectivity without phytotoxicity and decreased effects of organic solvents affecting to biological systems.

In addition, the herbicide formulation of the present invention is a labor saving herbicide and exhibits a wide spectrum for weed control since the herbicide formulation is a complex formulation comprising a herbicidally active ingredient of thiolcarbamate type and another herbicidally active ingredient for controlling broadleaf weeds, galingale weeds, or the like.

What is claimed is:

1. A complex suspended herbicide formulation comprising:

a herbicidally effective amount of an active ingredient of thiolcarbamate type which is liquid at common temperature;

a solid, herbicidally effective amount of an active ingredient which is slightly soluble in said herbicidally active ingredient of thiolcarbamate type at common temperature;

a surfactant; and a dry process white carbon;

wherein said solid herbicidally active ingredient is dispersed and suspended in said herbicidally active ingredient of thiolcarbamate type in the presence of said surfactant and said dry process white carbon.

2. A complex suspended herbicide formulation as recited in claim 1, wherein said herbicidally active ingredient of thiolcarbamate type is represented by the formula:

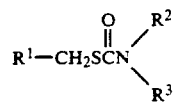

[I]

wherein $R^1$ is an alkyl group having from 1 to 3 carbon atoms, a phenyl group, or a halogen-substituted phenyl group; $R^2$ and $R^3$ are alkyl groups having from 1 to 5 carbon atoms, with the proviso that $R^2$ and $R^3$ may form a ring.

3. A complex suspended herbicide formulation as recited in claim 1, wherein said herbicidally active ingredient of thiolcarbamate type is S-(4-chlorobenzyl)-N,N-diethylthiol carbamate.

4. A complex suspended herbicide formulation as recited in claim 1, wherein said dry process white carbon is fine granulate silicic acid produced by pyrolysis of a halogenated silicon, a compound containing a silicic acid, or an organosilicon compound.

5. A complex suspended herbicide formulation as recited in claim 1, wherein said herbicidally active ingredient of thiolcarbamate type is S-(4-chlorobenzyl)-N,N-diethylthiolcarbamate, said solid, herbicidally active ingredient is methyl=α-(4,6-dimethoxypyrimidin-2-ylcarbamoylsulfamoyl-O-toluate), and said surfactant is polyoxyethylene styrylphenyl ether.

* * * * *